US010125402B2

(12) United States Patent
Baum et al.

(10) Patent No.: US 10,125,402 B2
(45) Date of Patent: Nov. 13, 2018

(54) METHOD FOR MEASURING CELL-FREE VIRUS PARTICLES FROM DRIED BLOOD SPOTS

(71) Applicant: Roche Molecular Systems, Inc., Pleasanton, CA (US)

(72) Inventors: Paul Baum, San Francisco, CA (US); Megan M. Crask, Livermore, CA (US); Xiaoning Wu, Fremont, CA (US)

(73) Assignee: ROCHE MOLECULAR SYSTEMS, INC., Pleasanton, CA (US)

( * ) Notice: Subject to any disclaimer, the term of this patent is extended or adjusted under 35 U.S.C. 154(b) by 92 days.

(21) Appl. No.: 14/518,150

(22) Filed: Oct. 20, 2014

(65) Prior Publication Data

US 2015/0232955 A1    Aug. 20, 2015

Related U.S. Application Data

(60) Provisional application No. 61/894,332, filed on Oct. 22, 2013, provisional application No. 62/025,886, filed on Jul. 17, 2014.

(51) Int. Cl.
*C12Q 1/70* (2006.01)
*G01N 1/34* (2006.01)

(52) U.S. Cl.
CPC .............. *C12Q 1/703* (2013.01); *G01N 1/34* (2013.01)

(58) Field of Classification Search
None
See application file for complete search history.

(56) References Cited

U.S. PATENT DOCUMENTS

| 4,752,565 A | 6/1988 | Folks et al. | |
| 8,497,112 B2 * | 7/2013 | Kistner ................ | A61K 39/145 435/235.1 |
| 2004/0241654 A1 | 12/2004 | Das et al. | |
| 2010/0240023 A1 | 9/2010 | Hermet et al. | |

FOREIGN PATENT DOCUMENTS

| FR | 2901281 A1 | 11/2007 |
| WO | 1999011764 A3 | 6/1999 |
| WO | 2007135332 A1 | 11/2007 |
| WO | 2008/064684 A1 | 6/2008 |
| WO | 2008066858 A2 | 6/2008 |
| WO | 2008/137868 A1 | 11/2008 |
| WO | 2010091080 A2 | 8/2010 |
| WO | 2013144743 A1 | 10/2013 |
| WO | PCT/EP2014/072386 | 2/2015 |

OTHER PUBLICATIONS

Fischer et al. (Journal of Clinical Microbiology, 2004, vol. 42, p. 16-20).*
McCabe (PCR methods and Applications, p. 99-106).*
Corran et al. (Malaria Journal, 2008, p. 1-12).*
Wu et al. (Journal of Clinical Virology, 2015, p. 38-40).*
Cobas, 2007, package insert for HIV-1 PCR.*
Sizmann et al. (Journal of Clinical Virology, 2010, p. 41-46).*
Walter et al. (Gene Expression, 2009, p. 15-16).*
Roche Diagnostics (2008, p. 1-2).*
Begolo et al. (Lab Chip, Sep. 17, 2013, vol. 13, p. 4331-4342).*
Mohamed et al. (PLOS, 2013, Apr. 16, p. 1-7.*
Parker (Journal of Clinical Pathology, 1999, vol. 52, p. 633-639).*
Mohamed S et al., Dried Blood Spot Sampling for Hepatitis B Virus Serology and Molecular Testing, PLoS ONE, Apr. 16, 2013, p. e61077: 1-7, vol. 8, No. 4.
De Vries, Jutte J.C., et al., 2009, "Evaluation of DNA extraction methods for dried blood spots in the diagnosis of congenital cytomegalovirus infection", Journal of Clinical Virology, 46s:s37-s42.
Gohring, Katharina, et al., 2010, "Influence of different extraction methods and PCR techniques on the sensitivity of HCMV-DNA detection in dried blood spot (DBS) filter cards", Journal of Clinical Virology, 48:278-281.
Mitchell, Caroline, et al., 2008, "Diminished Human Immunodeficiency Virus Type 1 DNA Yield from Dried Blood Spots after Storage in a Humid Incubator at 37 degrees Celsius Compared to −20 degrees Celsius", Journal of Clinical Microbiology, 46(9):2945-2949.
Soetens, Oriane, et al., 2008, "Evaluation of Different Cytomegalovirus (CMV) DNA PCR Protocols for Analysis of Dried Blood Spots from Consecutive Cases of Neonates with Congenital CMV Infections", Journal of Clinical Microbiology, 46(3):943-946.
Arredondo et al. Comparison of HIV-1 RNA Measurements Obtained by Using Plasma and Dried Blood Spots in the Automated Abbott Real-Time Viral Load Assay. J. Clin. Microbiol. 2012, 50(3):569.
Baum, P. & Heilek, G., Viral load monitoring: shifting paradigms in clinical practice. MLO Med Lab Obs. Nov. 2013;45 (11):8, 10, 12.
Bertagnolio, S. et al., Dried blood spots for HIV-1 Drug Resistance and Viral Load Testing: A Review of Current Knowledge and Who Efforts for Global HIV Drug Resistance Surveillance. 2010 AIDS Rev. 12:195-208.
Blankson, et al. The Challenge of Viral Reservoirs in HIV-1 Infection. 2002. Annu. Rev. Med. 53:557-593.
Folks TM, et al. Biological and biochemical characterization of a cloned Leu-3-cell surviving infection with the acquired immune deficiency syndrome retrovirus. 1986. J Exp Med. 164:280-290.
Greene, W.C. and Peterlin, B.M., Charting HIV's remarkable voyage through the cell. 2002. Nat Med. 8(7): 673-80.
Johannessen, A., Dried blood spots in HIV monitoring: applications in resource-limited settings. 2010. Bioanalysis. 2 (11):1893-1908.
Johanson, et al. DNA elution from buccal cells stored on Whatman FTA Classic Cards using a modified methanol fixation method. 2009. BioTechniques. vol. 46 No. 4, 309-311.

(Continued)

*Primary Examiner* — Agnieszka Boesen
(74) *Attorney, Agent, or Firm* — Eric Grant Lee

(57) ABSTRACT

Methods for the measuring cell-free nucleic acids and/or virus particles from dried blood spots are described. The methods can include the steps of rehydrating a dried blood sample, optionally fixing cells present in the rehydrated dried blood sample, eluting cell-free virus particles from the rehydrated dried blood sample, separating the cell-free viruses from any cell debris that may be present in the rehydrated dried blood sample by way of a filter, and measuring cell-free virus particles by a viral particle quantification technique.

15 Claims, 6 Drawing Sheets

(56) References Cited

OTHER PUBLICATIONS

Smit, PW et al. Systematic review of the use of dried blood spots for monitoring HIV viral load and for early infant diagnosis. 2014. PLoS ONE. 9(3): e86461.

Wu, et al. A simple method to elute cell-free HIV from dried blood spots improves the ascertainment of virologic expression. AIDS 2014 Abstract (Jul. 20-25, 2014).

Luo, "Improving Solutions for Viral Load Monitoring in Resource Limiting Settings" Presentation for Educational Symposium at 2014 International AIDS Conference (Jul. 20-25, 2014).

Corran, et al., Supplementary file I, "Dried blood spots as a source of anti-malarial antibodies for epidemiological studies," Malaria Journal 7:195 (2008).

Corran, et al., Additional File I, "Dried blood spots as a source of anti-malarial antibodies for epidemiological studies," Malaria Journal 7:195 (2008).

Liu, Shiguo, et al., Chinese Journal of Cellular and Molecular Immunology 27(6):647-649 (2011).

State Intellectual Property Office, P.R. China, English Translation of Office Action for CN 201480057848.6 (dated Apr. 18, 2017).

\* cited by examiner

METHOD FOR MEASURING CELL-FREE VIRUS PARTICLES FROM DRIED BLOOD SPOTS

CROSS REFERENCE TO RELATED APPLICATIONS

This application claims the benefit of priority of U.S. Provisional Patent Application Ser. Nos. 61/894,332 filed Oct. 22, 2013, 61/945,974 filed Feb. 28, 2014, and 62/025,886 filed Jul. 17, 2014, which are incorporated herein by reference in their entirety.

FIELD OF THE INVENTION

The present invention relates to the field of measuring viral load in blood, and more particularly, to methods for measuring cell-free virus particles from dried blood spots.

BACKGROUND OF THE INVENTION

In 2013, the World Health Organization (WHO) revised the current HIV treatment and prevention guidelines and emphasized the importance of HIV viral load (VL) testing in the management of HIV positive patients. Instead of clinical presentations and CD4 cell counts, WHO strongly recommends using HIV viral load testing to monitor the HIV Antiretroviral Therapy (ART) and dropped the cutoff of the level of HIV plasma VL from 5000 copies/mL to 1000 copies/mL for therapeutic efficacy. In other words, if HIV patients under ART have a viral titer in plasma is greater than 1000 copies/mL, it will be considered as a drug treatment failure. Responses to treatment failure, such as adherence counseling, drug resistance testing and second line treatment regimens, are time-consuming and expensive, and should be used only if necessary.

After infection, HIV virus not only starts to replicate itself in the infected cells, but also integrates its cDNA into the host chromosomes as the latent HIV proviral DNA (Greene, W. C. and Peterlin, B. M. 2002. Charting HIV's remarkable voyage through the cell. Nat Med. 8(7): 673-80; Blankson, J. N., D. Persaud, R. F. Siliciano. 2002. The Challenge of Viral Reservoirs in HIV-1 Infection. Annu. Rev. Med. 53:557-593). HIV viral load is normally measured using plasma as a specimen type. However, in resource limited settings, such as Africa, plasma samples may not be easily obtained, stored, transferred, and tested (World Health Organization. 2013. Consolidated guidelines on the use of antiretroviral drugs for treating and preventing HIV infection: recommendations for a public health approach. World Health Organization, Geneva). Dried blood spots (DBS) have been evaluated as a solution for HIV viral load testing in the resource limited settings, with limited success (Smit P W et al. 2014. Systematic review of the use of dried blood spots for monitoring HIV viral load and for early infant diagnosis. PLoS ONE. 9(3): e86461; Bertagnolio, S., N. T. Parkin, M. Jordan, J. Brooks, J. G. Garcia-Lemia. 2010; Dried blood spots for HIV-1 Drug Resistance and Viral Load Testing: A Review of Current Knowledge and WHO Efforts for Global HIV Drug Resistance Surveillance. AIDS Rev. 12:195-208; Johannessen, A. 2010; Dried blood spots in HIV monitoring: applications in resource-limited settings. Bioanalysis. 2(11):1893-1908). Roche Molecular Diagnostics (RMD) has a research use only (RUO) product, developed in 2009, which uses the real-time PCR COBAS® AmpliPrep/COBAS® TaqMan® (CAP/CTM) HIV-1 Test v2.0 and Dried Fluids Spot Procedure (DFSP), to measure the HIV viral load in DBS. Unfortunately, when paired plasma and DBS samples are tested, the DFSP test yields higher viral load titers compared to the plasma gold standard. This overestimation is particularly pronounced in samples with plasma viral loads less than 5,000 copies/mL, presumably due to the detection of cell-associated HIV DNA and RNA.

According to the CAP/CTM HIV-1 DFSP procedure, HIV DBS is first incubated with a chaotropic agent—Specimen Pre-Extraction (SPEX) buffer and the total nucleic acids, including HIV viral RNA in blood fluids, plus other cell-associated HIV DNA and RNA, such as HIV proviral DNA, are extracted and eluted from DBS into the SPEX buffer. Then, the extracted buffer is placed on the CAP/CTM instrument for nucleic acid purification followed by HIV target amplification and detection. The currently existing nucleic acid extraction methodologies for HIV DBS VL measurement fully lyse all cells and denature all protein complexes, allowing the complete extraction of total nucleic acids from DBS, including free HIV viral particles in blood fluids and cell-associated HIV RNA and DNA.

Over-quantification of HIV VL in DBS is a problem not only with Roche's DBS assay, but also observed with other commercially available assays, such as Abbott's HIV DBS assay. In HIV scientific and medical communities, it has been speculated that HIV DNA present in HIV infected cells in the DBS causes the over quantification of the viral load, although the exact mechanisms of this over quantification phenomenon are not clear or demonstrated (Médecins Sans Frontieres Access Campaign, 2013). The overestimation in DBS may be ameliorated but not eliminated by amplification procedures that have specificity for RNA over DNA (e.g., the NASBA procedure used by BioMerieux NucliSENS®). There remains a need for alternative procedures for addressing the challenges of HIV VL over-quantification in a sample.

SUMMARY OF THE INVENTION

One solution for the overestimation in DBS can be to remove both cell-associated RNA and DNA from the sample, leaving only the cell-free virus to be detected, similar to a plasma sample. This can prevent the costly misclassification of patients as treatment failures. Such methods and related benefits are described in the present disclosure.

In one embodiment, a method for measuring cell-free nucleic acids and/or virus particles from dried blood spots is provided. The method may include the steps of rehydrating a dried blood sample by applying a buffer solution to the dried blood sample to produce a rehydrated dried blood sample; optionally, fixing cells present in the rehydrated dried blood sample with a fixing reagent to contain cell-associated RNA and/or DNA with the cells; eluting cell-free nucleic acids and/or virus particles from the rehydrated dried blood sample with an eluting reagent that preferentially elutes cell-free virus particles without disrupting the cell-associated RNA and/or DNA; separating the cell-free nucleic acids and/or virus particles from any cell debris that may be present in the rehydrated dried blood sample by way of a filter; and measuring cell-free nucleic acids and/or virus particles by a viral particle quantification technique selected from the group consisting of sequence-specific nucleic acid quantification, enzyme-linked immunosorbent assay (ELISA), polymerase chain reaction (PCR), isothermal nucleic acid amplification, nucleic acid hybridization, in situ hybridization, and electron microscopy.

In some embodiments, the virus particles to be measured in the DBS can be one or more of human immunodeficiency virus (HIV), human T-cell lymphotropic virus-1 or -2 (HTLV-1, or -2), hepatitis C virus (HCV), hepatitis B virus (HBV), cytomegalovirus (CMV) (e.g., human CMV), and Epstein-Barr virus (EBV). An embodiment of the buffer solution may include a fixing reagent and an eluting reagent. One embodiment of the fixing reagent can be methanol and one embodiment of the eluting reagent can be phosphate buffered saline or other suitable buffers. In some embodiments of the method, the separation step may include spin column filtration, vacuum filtration, or centrifugation. Embodiments may include a filter having pore sizes with a range of between about 0.1 µm to about 100 µm, e.g., between about 20 µm to about 80 µm, e.g., between about 30 µm to about 70 µm, e.g., between about 40 µm to about 60 µm.

In another embodiment, the buffer solution comprises PBS. In an additional embodiment, the buffer solution comprises the eluting solution. In one other embodiment, the eluting solution comprises PBS.

The details of one or more embodiments of the invention are set forth in the accompanying drawings and the description below. Other features, objects, and advantages of the invention will be apparent from the drawings and detailed description, and from the claims.

DETAILED DESCRIPTION OF THE INVENTION

Figure 1:
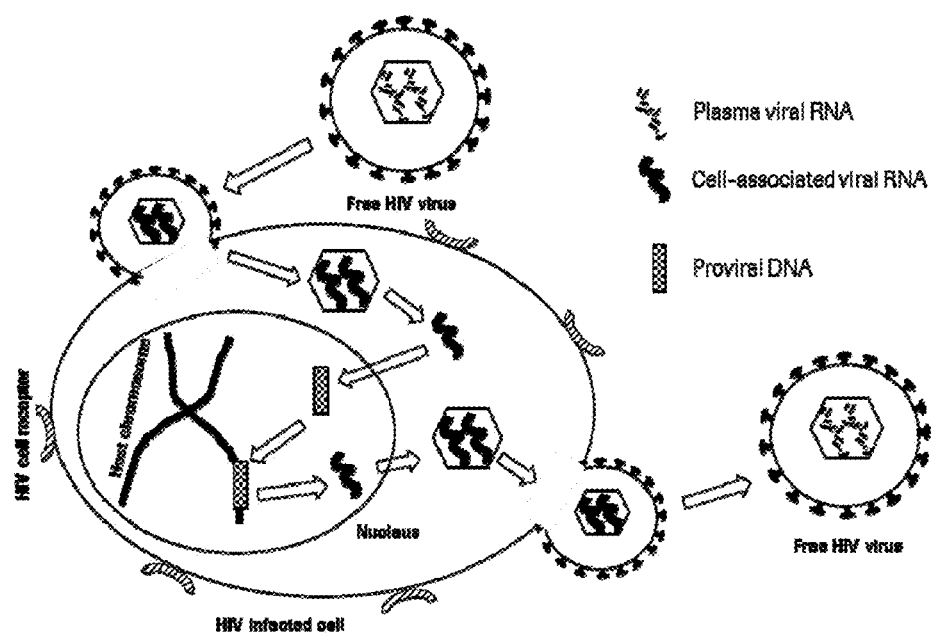
FIG. 1 shows a schematic view of the life cycle of HIV virus. After a host cell is infected by HIV virus, the viral RNA genome is reverse transcribed by the viral encoded reverse transcriptase to cDNA. The cDNA is then integrated into the host chromosomal DNA, which forms a proviral DNA. Additional HIV viral RNA genomes are transcribed from the proviral DNA and transported to the cytoplasm for viral particle assembling. The matured HIV virus buds out from the infected cells and becomes a free viral particle.
Figure 2:
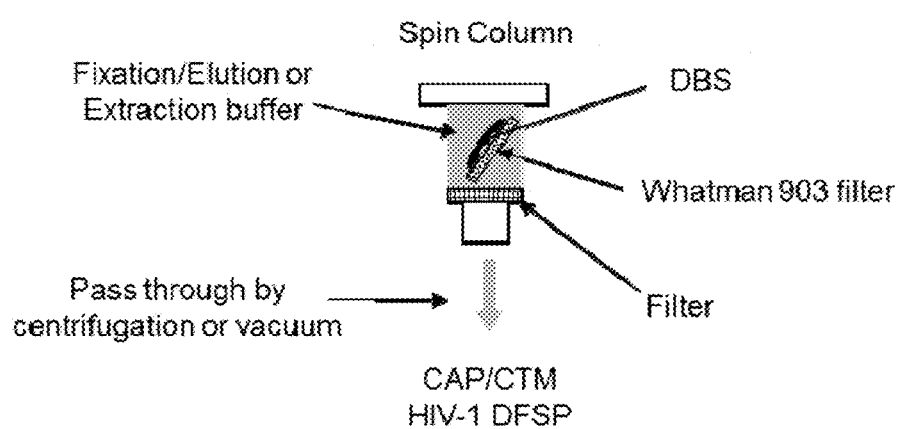
FIG. 2 shows a schematic view of an exemplary embodiment of a set up for measuring cell-free virus particles from dried blood spots. An HIV patient's sample with DBS on Whatman filter paper is first placed into a spin column and incubated with a fixation/elution or extraction buffer. After extraction of viral particles from DBS, the buffer containing the viruses is passed through a filter in the spin column by, e.g., either centrifugation or vacuum. The collected pass through buffer is then placed on the CAP/CTM for further sample preparation and target amplification and detection.
Figure 3:
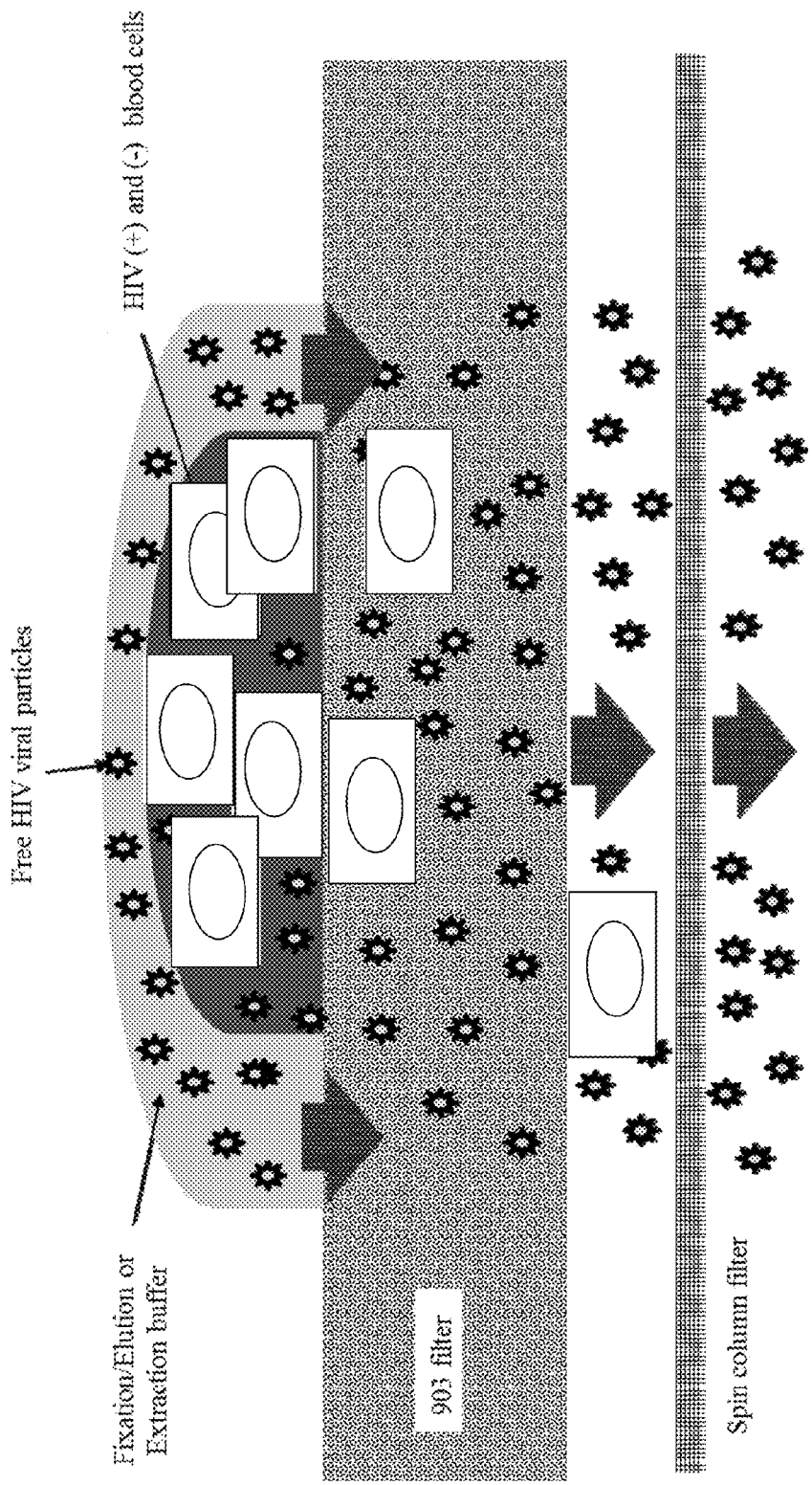
FIG. 3 shows a detailed schematic view of an exemplary embodiment of a method for measuring cell-free virus particles from fixed DBS on Whatman 903 filter paper. Upon the rehydration and fixation, most of blood cells remain on the surface of the filter paper and cell-associated HIV DNA and RNA are contained in the infected cells, while cell-free viral particles are defused into the elution buffer. Some blood cells including HIV infected cells and cell debris may also dissociate with the 903 filter paper. When centrifugation is performed, the spin column filter prevents the cells or cell debris from passing through, but not the eluted cell-free viruses, and cell-free HIV viruses are collected from the pass through solution.

While products are available that reduce the contribution of cell-associated DNA to DBS viral load measurement, the methods described herein can reduce both cell-associated RNA and cell-associated DNA. The described procedures are easy to operate and do not require complicated instrumentation and biochemical treatments. Importantly, the methods do not alter the currently existing sample collection methods for DBS, or change the existing downstream protocols, e.g., RMD CAP/CTM HIV-1 DFSP product.

Rehydrating a DBS (e.g., an HIV DBS) with a solution or extraction buffer that can only elute out the cell-free viral particles (e.g., cell-free HIV viral particles) from the rehydrated DBS without disrupting cells or cell debris on the DBS can allow separation of the smaller cell-free particles from the larger cell-associated debris. Measuring viral load (VL) (e.g., HIV VL) from the freed virus particles can then be done without interference from the cell-associated RNA and DNA (e.g., HIV RNA and DNA).

In one aspect of the invention, a DBS (e.g., an HIV DBS) is rehydrated in a buffer solution. In one embodiment, the buffer solution comprises a biological buffer and a fixing reagent. For example, phosphate buffered saline (PBS) (the biological buffer) with methanol (the fixing reagent) may be used, which can preferentially elute cell-free viral particles (e.g., cell-free HIV particles), but not disrupt the infected cells (e.g., HIV infected cells with cell-associated HIV RNA and proviral DNA) in a rehydrated DBS (e.g., an HIV DBS). Exemplary embodiments of the fixative and dehydrant reagents, such as methanol, ethanol, formaldehyde, chloroform, and/or acetone may be used. Exemplary embodiment of the eluting buffer may include phosphate buffered solutions, such as PBS. PBS is a normal buffer that is close to the human physiological conditions and methanol is able to fix cells by precipitating proteins. Methanol has widely been used as a gentle fixative in immunoassays. When a DBS (e.g., an HIV DBS) is treated with PBS plus methanol, the cell-associated viral RNA and DNA (e.g., HIV RNA and DNA) can be contained in the fixed cells, while the cell-free viral particles (e.g., HIV particles) can be eluted out from the PBS rehydrated DBS. Although the cell-free virus recovery rate with this PBS/methanol solution may be lower than that with SPEX buffer, this solution may be able to significantly decrease the release of the cell-associated viral DNA and RNA (e.g., HIV DNA and RNA) from DBS (see Examples). Optimizing the experimental protocols and procedures can increase the virus recovery rate from DBS. In addition, other buffers and their combinations with solvents that have the similar properties as PBS/methanol can be used in some embodiment of the described methods.

In another aspect of the invention, a DBS (e.g., an HIV DBS) is rehydrated in a buffer solution in the absence of a fixing reagent. In one additional embodiment, the DBS is rehydrated in a buffer solution comprising a biological buffer. In another embodiment, the biological buffer is PBS. In one other embodiment, the buffer solution is free of a fixing reagent. The PBS-containing buffer solution may be used to preferentially elute cell-free viral particles (e.g., cell-free HIV viral particles) without disruption of infected cells (e.g., HIV infected cells containing cell-associated HIV RNA and proviral DNA) that are present in the rehydrated DBS. When DBS is treated with PBS, the cell-associated RNA and DNA can be contained in the fixed cells, while the cell-free viral particles can be eluted out from the PBS rehydrated DBS. In one embodiment, the DBS is an HIV DBS.

In an additional aspect, the present invention provides a method for measuring cell-free virus particles from a dried blood spot (DBS). In one embodiment, the method comprises the step of rehydrating a dried blood sample by applying a buffer solution to the dried blood sample to produce a rehydrated dried blood sample. In another embodiment, the method comprises the step of eluting cell-free virus particles from the rehydrated dried blood sample with an eluting reagent. In one other embodiment, the eluting reagent preferentially elutes cell-free virus particles without disrupting the cell-associated RNA and/or DNA. In one additional embodiment, the method comprises the step of separating the cell-free viruses from any cell debris that may be present in the rehydrated dried blood sample. In one embodiment, the separation is by way of a filter. In one other embodiment, the step of separating is optional. In another embodiment, the method comprises the step of measuring cell-free virus particle by a viral particle quantification technique. In one other embodiment, the virus particles are RNA or DNA virus particles. In an additional embodiment, the RNA or DNA virus particles are present in an aqueous solution during the rehydrating step (the aqueous buffer solution) and during the eluting step (the aqueous eluting solution) such that they are suitable for use in the separating and/or the measuring steps of the method.

To further reduce the contamination of the cell-associated viral (e.g., HIV) RNA and DNA from the rehydrated DBS, the PBS/methanol (or PBS alone) extracted eluates can be passed through a filter, which allows further separation of the eluted virus particles from any larger cell debris that have possibly fallen out from the DBS during the extraction. Spin column filters are available with defined pore sizes. Other separation methods, such as vacuum filtration or centrifugation, may increase the throughput of this method. Those of ordinary skill in the art will appreciate that other methods for separation may be suitable. In one embodiment, the DBS is an HIV DBS.

The described methods of the present application can also be applied for isolation of other blood-borne viruses from DBS or whole blood, such as HTLV, HCV, HBV, or the like. Furthermore, the methods can be extended to isolate small biochemical molecules, such as small nucleic acids or polypeptides, from large cells or cell debris. For example, the methods can be used to collect cell-free tumor specific nucleic acids or antigens from whole blood without interferences of large amounts of chromosomal DNA and cell debris. The methods can also be used to enrich for circulating fetal DNA from maternal DBS samples.

The periodic measurement of viral load is an important tool for guiding the treatment regimens of infected individuals, especially those on anti-viral therapy (e.g., anti-retroviral therapy) (Arredondo et al. J. Clin. Microbiol. 2012, 50(3):569). As discussed herein, the measurement of viral load in plasma faces certain challenges in resource-limited settings and the measurement of viral load in dried blood samples has met with limited success. The methods of the present invention can be used to obtain a viral load measurement from a dried blood sample that is in concordance with a viral load (VL) measurement from a plasma sample. The term "concordance" or "concordant with" as used herein refers to the degree that at least two viral load measurements are in a state of statistical agreement. In some embodiments, the concordance of a dried blood sample VL measurement with a plasma VL measurement is between about 85% and about 99%. In other embodiments, the concordance is at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, This type of concordance applies in the context of a medical decision point for a patient before, during, or after anti-viral therapy. At a medical decision point, it is common to measure HIV viral load in a patient sample by the $\log_{10}$ of the number of virus copies (cp) per mL (or $\log_{10}$ cp/mL). In general, the cutoff for HIV viral load (VL) is 1000 cp/mL, where a >1000 cp/mL or <1000 cp/mL measurement guides a medical decision. For instance, depending on the cp/mL measured, the medical decision might be initiating an HIV treatment regimen, as well as continuing, modifying, or ceasing an existing HIV treatment regimen. For example, for an HIV patient receiving anti-retroviral therapy, a subsequent measurement of >1000 cp/mL of HIV would indicate that the existing therapy has not been successful while a measurement of <1000 cp/mL of HIV would indicate that the existing therapy has been successful. Therefore, concordance between viral load measurements from a dried blood sample and from a plasma sample means that the cp/mL demonstrate a statistically significant correlation in the context of a medical decision point. As described in Example 3 Table 3.2, paired samples from 196 patient samples were used to obtain viral load measurements from a plasma sample, and from a dried blood sample process according to the methods of the present invention (also referred to as a Free Virus Elution or FVE process). Out of 196 paired samples, (i) 93 were found to have a VL of <1000 cp/mL for both plasma and dried blood sample; (ii) 93 were found to have a VL of >1000 cp/mL for both plasma and dried blood sample; and (iii) only 10 were found to have >1000 cp/mL in plasma and <1000 cp/mL in dried blood sample. As such, the overall dried blood sample concordance with plasma was high at 95%. By contrast and as shown in Table 3.1, the overall dried blood sample concordance with plasma using the dried fluid spot protocol (DFSP) was much lower due to the fact that out of 196 paired samples, 64 were found to have >1000 cp/mL in plasma but <1000 cp/mL in dried blood sample. As such, the overall dried blood sample concordance with plasma was only at 67%.

In another aspect, the present invention provides methods in which the HIV viral load (VL) measurement cutoff for purposes of guiding a medical decision is between about 1000 cp/mL and about 5000 cp/mL, wherein a VL measurement>the cutoff would indicate that an existing therapy has not been successful, while a VL measurement<the cutoff would indicate that an existing therapy has been successful. In other embodiments, the VL measurement cutoff is about 1100 cp/mL, about 1200 cp/mL, about 1300 cp/mL, about 1400 cp/mL, about 1500 cp/mL, about 1600 cp/mL, about 1700 cp/mL, about 1800 cp/mL, about 1900 cp/mL, about 2000 cp/mL, about 2100 cp/mL, about 2200 cp/mL, about 2300 cp/mL, about 2400 cp/mL, about 2500 cp/mL, about 2600 cp/mL, about 2700 cp/mL, about 2800 cp/mL, about 2900 cp/mL, about 3000 cp/mL, about 3100 cp/mL, about 3200 cp/mL, about 3300 cp/mL, about 3400 cp/mL, about 3500 cp/mL, about 3600 cp/mL, about 3700 cp/mL, about 3800 cp/mL, about 3900 cp/mL, about 4000 cp/mL, about 4100 cp/mL, about 4200 cp/mL, about 4300 cp/mL, about 4400 cp/mL, about 4500 cp/mL, about 4600 cp/mL, about 4700 cp/mL, about 4800 cp/mL, about 4900 cp/mL, or about 5000 cp/mL.

In one aspect, the present invention provides a method for obtaining a viral load measurement from a dried blood sample that is in concordance with a viral load measurement from a plasma sample. In another aspect, the present invention provides a method for measuring cell-free virus particles from dried blood samples (e.g., dried blood spots). In one embodiment, the method comprises the step of rehydrating a dried blood sample with a buffer solution. In another embodiment, the dried blood sample is suspected of containing virus particles. In other embodiments, the buffer solution comprises PBS. In an additional embodiment, the rehydrating step is followed by an eluting step.

In another embodiment, the method comprises the step of eluting cell-free virus particles from the rehydrated dried blood sample with an eluting reagent that preferentially elutes cell-free virus particles without disrupting cell-associated nucleic acid (or elutes cell-free virus particles in the absence of disrupting cell-associated nucleic acid). In one embodiment, cell-associated nucleic acid is RNA and/or DNA. In an additional embodiment, the eluting reagent is the same as the buffer solution from the rehydrating step. In an additional embodiment, the eluting step is followed by a separating step.

In another embodiment, the method comprises the step of incubating a dried blood sample in a buffer solution to rehydrate the dried blood sample and elute cell-free virus particles without disrupting cell-associated nucleic acid (or elute cell-free virus particles in the absence of disrupting cell-associated nucleic acid). In an additional embodiment, the incubating step is followed by a separating step.

In one other embodiment, the method comprises the step of separating the cell-free virus from the rehydrated dried blood sample. In one embodiment, the separating step comprises separating the cell-free virus from any cell debris that may be present in the rehydrated dried blood sample. In another embodiment, the separating step comprises filtration, including, without limitation, spin column filtration by centrifugation or vacuum. In some embodiments, the filtration comprises use of a filter having a pore size of between about 0.1 µm to about 100 µm. In an additional embodiment, the separating step is preceded by a rehydrating step and/or an eluting step, or preceded by an incubating step.

In one aspect, the method comprises a measuring step based on the sample obtained from the separating step. In one embodiment, the measuring step comprises measuring the amount of cell-free virus particles in the sample obtained after the separating step. In another embodiment, the measuring step comprises obtaining a viral load measurement from the sample that is in concordance with a viral load measurement from a plasma sample. In one other embodiment, the measuring step comprises viral particle quantification. In some embodiments, a virus particle quantification technique is selected from the group consisting of sequence-specific nucleic acid quantification, ELISA, PCR, isothermal nucleic acid amplification, nucleic acid hybridization, in situ hybridization, and electron microscopy. Those of ordinary skill in the art will appreciate that other virus particle quantification techniques may be suitable for use with the methods described herein.

In one embodiment, the methods described herein are suitable for measuring various viruses, including without limitation, HIV, HTLV, HCV, HBV, CMV, and EBV.

As described herein, the CAP/CTM HIV-1 Test Dried Fluid Spot Procedure involves the incubation of a dried blood sample with a chaotropic agent (SPEX buffer) to extract nucleic acid. This procedure also requires incubation of the sample in the buffer at 56° C. at 1000 rpm with continuous shaking for 10 minutes. In one aspect, the present invention provides methods of extracting cell-free viruses from a dried blood sample wherein the use of heating or elevated temperatures and vortexing or shaking are optional or not required. In one embodiment, the methods described herein are performed in the absence of heating or elevated temperature and/or in the absence of vortexing or shaking. In another embodiment, at least one or all of the steps of rehydrating, eluting, incubating, and separating are performed (i) without or in the absence of heating or elevated temperature; (ii) in the absence of or without vortexing or shaking; and/or (iii) at ambient temperature. The term "ambient temperature" refers to the temperature at which a dried blood sample is contacted with a buffer according to the methods of the present invention. Generally, the ambient temperature is the temperature of a temperature-controlled environment. Ambient temperature ranges from about 18° C. to about 30° C. In one embodiment, ambient temperature is about 18° C., about 19° C., about 20° C., about 21° C., about 22° C., about 23° C., about 24° C., about 25° C., about 26° C., about 27° C., about 28° C., about 29° C., or about 30° C.

In one other embodiment, the DBS to be rehydrated comprises EDTA-whole blood. EDTA has beneficial properties when used in blood samples including, without limitation, a preservative, an anti-coagulant, and/or an antibacterial. Those of ordinary skill in the art will appreciate that other preservatives/anti-coagulants/antibacterial agents may be suitable for use in a blood sample and its corresponding DBS that are the subject of the methods described herein.

Embodiments of the disclosures will be further described in the following examples, which do not limit the scope of the invention described in the claims.

EXAMPLES

The following examples and figures are provided to aid the understanding of the present invention, the true scope of which is set forth in the appended claims. It is understood that modifications can be made in the procedures set forth without departing from the spirit of the invention.

Example 1

Protocol:
1. Collect DBS samples to be tested using standard methods, spotting the blood onto a Whatman 903 filter card and allowing it to dry.
2. Cut out the dried blood spot from the Whatman filter card and place into an appropriately labeled S-tube or spin filter column.
3. Add 100 µL of the 10% methanol in PBS buffer to the tube containing the DBS. If adding to a spin column, add 500 µL of buffer only.
4. Place S-tube or spin filter column in incubator at 56° C., 1000 rpm, for 10 minutes
   a. If DBS was placed directly in an S-tube, skip step 4.
5. Briefly centrifuge the columns in a microcentrifuge (if using the VWR 0.2 µm centrifugal filter, spin for 5-10 minutes at a maximum speed of 5000×g). Then remove and dispose of the spin column and add 500 µL of buffer to the collection tube.
6 Load samples onto COBAS® AmpliPrep and start HI2DFSP96 protocol.

Materials:

COBAS® AmpliPrep/COBAS® TaqMan® 96; COBAS® AmpliPrep/COBAS® TaqMan® HIV-1 Test Dried Fluid Spot Procedure RUO Kit; Whatman 903 Filter Cards (Whatman CAT#95026-896); 10% methanol solution in PBS; and VWR Centrifugal filters. Cat. Num. 82031-356, 0.2 μm pore size.

Results:

The PBS buffer was evaluated with different salts and detergents, such as NaCl (3 M), Tween-20 (0.1%), Triton X-100 (0.1%), SDS (1%), and methanol (10%). SPEX is the positive control to compare with. In the experiments, SPEX buffer was simply replaced by different individual buffers. The S-tubes containing DBS were incubated at 56° C. for 10 min with shaking. After extraction, the regular CAP/CTM HIV-1 DFSP protocol was followed (see package insert for the "COBAS® AmpliPrep/COBAS® TaqMan® HIV-1 Test Dried Fluid Spot Procedure"). Since the concentrations of HIV virus spiked and HIV cells into whole blood (WB) was relatively low (about 500 cp/DBS or 7E3 cp/mL, 12 cells/DBS or 1.2E3 cells/mL) and the viral titers only showed as <400 cp/mL. So, Ct values of target was used to compare the different buffers instead of viral titers. Almost all QS in those samples behaved normally.

As shown in Table 1, PBS with 10% methanol was able to elute the HIV viral particles from the virus spotted WB DBS relatively efficiently as compared with SPEX buffer. The Ct delay with PBS/MeOH could be due to the suboptimal extraction and elution conditions.

TABLE 1

Elution of HIV viral Particles from DBS (6 replicates)

| | SPEX | PBS/MeOH |
|---|---|---|
| Average Ct. | 31.8 ± 0.44 | 34.15 ± 1.64 |
| positive | 3 | 6 |
| Number of undetected | 3* | 0 |

*samples called Invalid based upon QS

As shown in Table 2, PBS/MeOH was only able to elute some detectable traces of the cell-associated HIV DNA and RNA from the HIV cell spiked WB with delayed Cts as compared to SPEX. In other words, PBS/MeOH significantly reduced the elution of cell-associated HIV DNA and RNA from HIV cell spiked DBS.

TABLE 2

Elution of cell-associated HIV DNA/RNA (6 replicates)

| | SPEX | PBS/MeOH |
|---|---|---|
| Average Ct. | 30.5 ± 1.66 | 35.27 ± 1.81 |
| positive | 6 | 3 |
| Number of undetected | 0 | 3 |

When HIV viruses plus HIV positive cells were mixed together and spiked into WB, as shown in Table 3 SPEX was able to elute both efficiently, while PBS/MeOH was only able to elute out HIV viruses with the similar Ct to the one with HIV virus alone (Table 1)

TABLE 3

Elution of Virus + Cell Mixture (6 replicates)

| | SPEX | PBS/MeOH |
|---|---|---|
| Average Ct. | 29.58 ± 0.81 | 33.75 ± 0.99 |
| positive | 6 | 6 |
| Number of undetected | 0 | 0 |

Table 4 summarizes the Ct differences between the virus spiked DBS and both virus and cell spiked DBS. Clearly, there was a large Ct different when SPEX buffer was used because of the contribution from the HIV cells, while there was a much smaller Ct difference when PBS/MeOH buffer was used which suggests that PBS/MeOH only eluted out the cell free viruses regardless the presence of HIV cells in DBS.

TABLE 4

| | SPEX | PBS/MeOH |
|---|---|---|
| Virus | 31.8 | 34.15 |
| Mixture | 29.58 | 33.75 |
| Ct. Difference (Virus-Cell) | 2.22 | 0.4 |

REFERENCES

Johanson, H. C., V. Hyland, C. Wicking, R A. Sturm. 2009. DNA elution from buccal cells stored on Whatman FTA Classic Cards using a modified methanol fixation method. BioTechniques. Vol. 46 No. 4.; Médecins Sans Frontières Access Campaign. 2013. Putting HIV treatment to the test: A product guide for viral load and point-of-care CD4 diagnostic tools.; 8E5 Cell line Producing Aids Viral Antigens without producing infectious virus particles: U.S. Pat. No. 4,752,565; Cultured Viral Particles from SeraCare, Certificate of Analysis (Part No: PN-227; Lot #: 51884)

Example 2

Protocol:
1. Collect DBS samples to be tested using standard methods, spotting the HIV positive EDTA whole blood onto a Whatman 903 filter card and allowing it to dry for at least 3 hours. [Munktell cards also work].
2. Cut out the dried blood spot from the Whatman filter card and place into an appropriately labeled S-tube.
3. Add 1000 μL of the PBS buffer to the tube containing the DBS.
4. Incubate at ambient temperature for at least 30 minutes.
   a. Heat and shaking (optional)
   b. If desired, the incubation time can be increased to overnight.
5. Load samples onto COBAS® AmpliPrep and start HI2DFSP96 protocol.

Materials:

COBAS® AmpliPrep/COBAS® TaqMan® 96; COBAS® AmpliPrep/COBAS® TaqMan® HIV-1 Test Dried Fluid Spot. Procedure RUO Kit; Whatman 903 Filter Cards; PBS (Mediatech, Inc. and made by Corning Cellgro, CAT#21-040-CV).

Results:

Investigations of the method's performance used paired dried blood spots and plasma samples from 157 HIV-infected subjects with viral loads ranging from undetectable to >10⁵ copies/mL. The performance of the new method (PBS extraction) was compared with that of the old method (extraction with the SPEX guanidinium buffer). The plasma viral loads were used as the gold standard.

The DBS were made from EDTA-whole blood. Plasma viral loads were measured with the regular plasma CAP/CTM HIV-1 v2.0 protocol. The SPEX extraction followed the regular DFSP protocol, including incubation at 56° C. for 10 min with shaking. PBS elution of DBS was performed in S-tubes containing 1 mL PBS at room temperature, without shaking. Elution times varied from 30 minutes to overnight. After extraction, the regular target amplification and detection under the CAP/CTM HIV-1 DFSP protocol was followed (see package insert for the "COBAS® AmpliPrep/ COBAS® TaqMan® HIV-1 Test Dried Fluid Spot Procedure").

Figure 4:
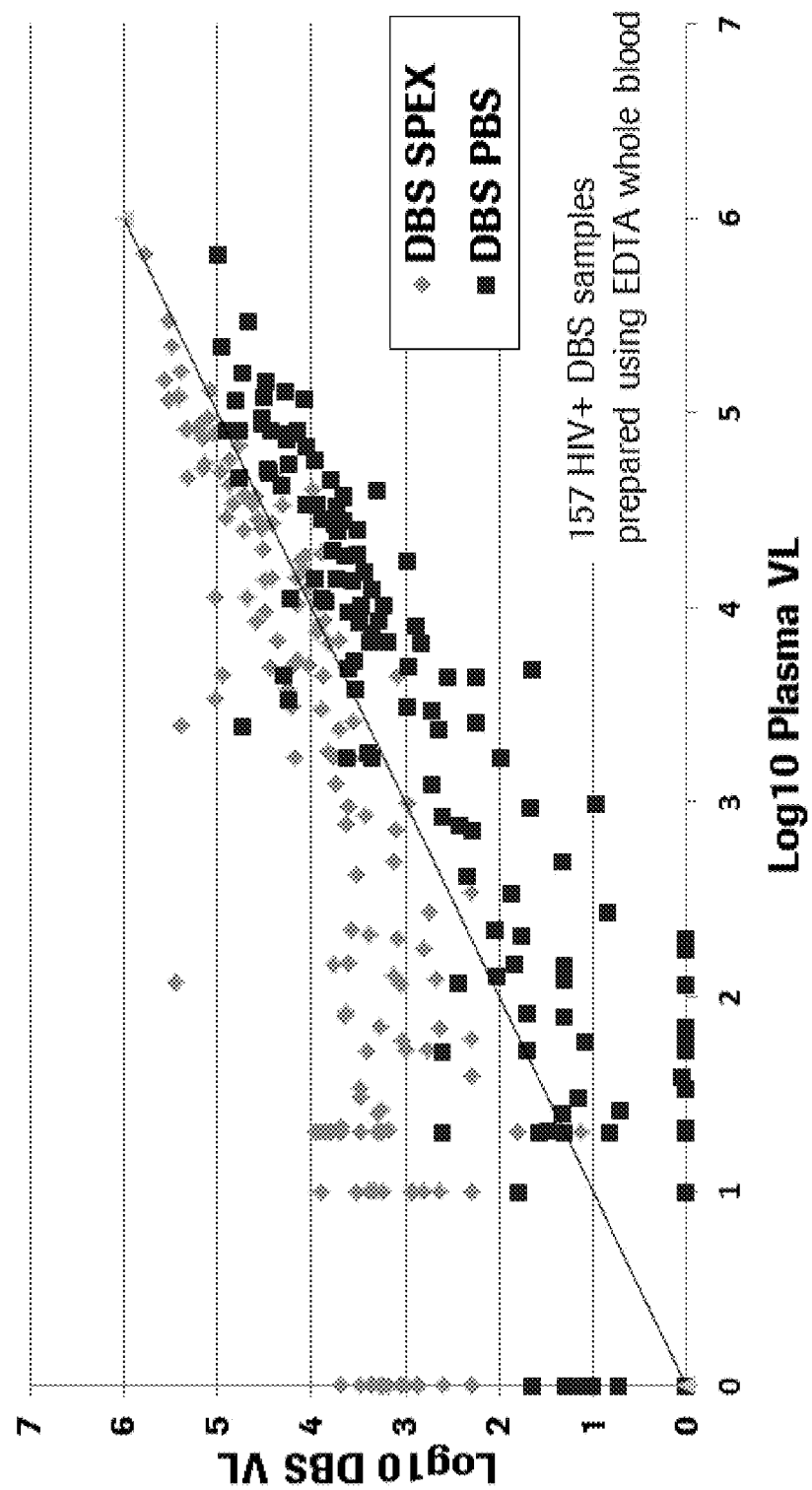
FIG. 4 shows the analytical performance of SPEX and PBS elution of dried blood spots, relative to plasma viral load.

As shown in FIG. 4, the DFSP method resulted in over-quantification of samples with low plasma viral loads. By contrast, the Free Virus Elution method showed much less over-quantification in this range. The Free Virus Elution method did result in a systematic under-quantitation across the test range of approximately 0.6 $\log_{10}$. Some of this under-quantitation, 0.3 $\log_{10}$ can be explained by the fact that whole blood is only 50% plasma, and the test definition file being used does not take this factor into account.

Figure 5:
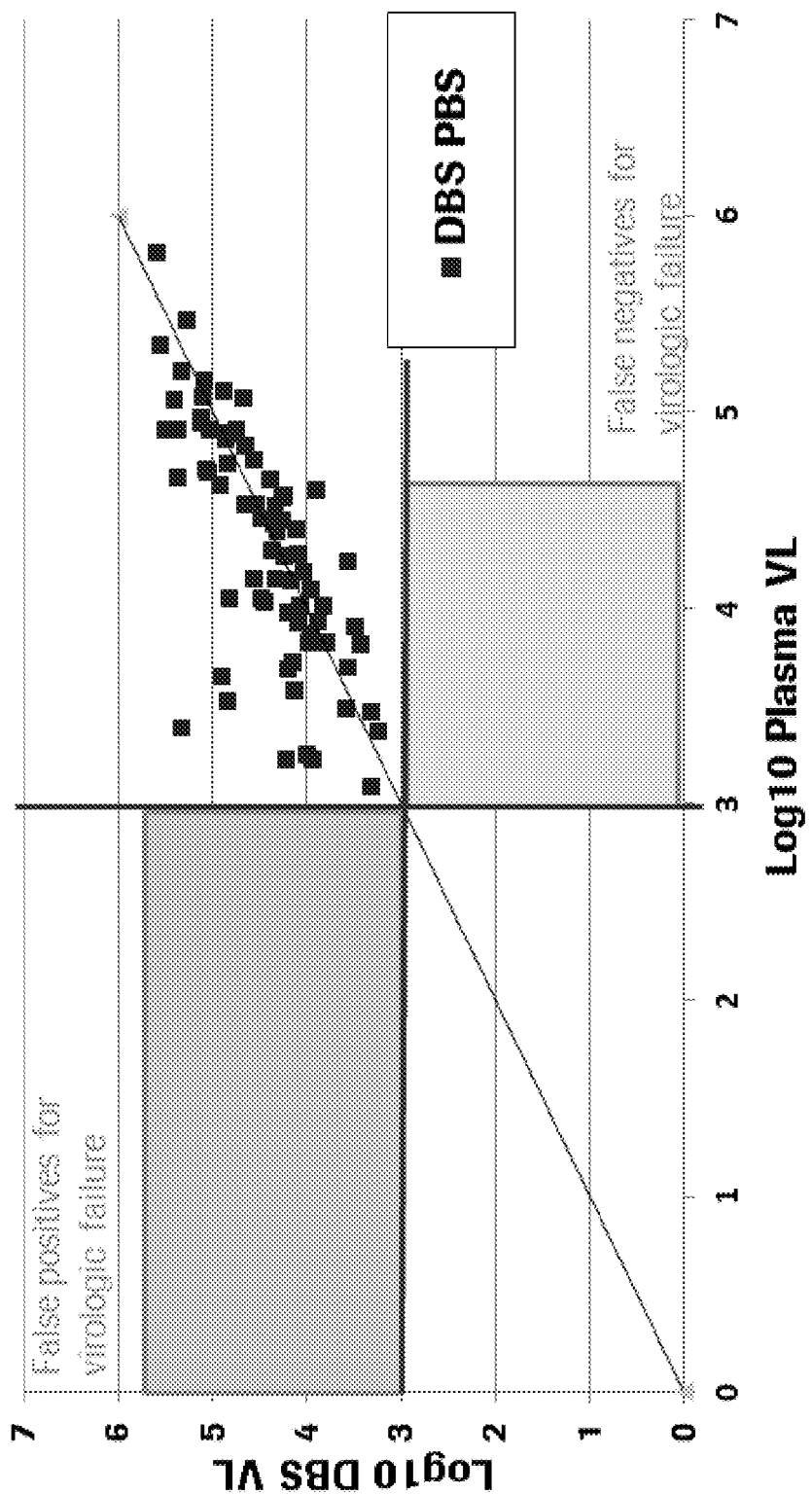
FIG. 5 shows the clinical correlation between DBS and plasma viral loads, using PBS elution. A correction factor of 0.6 log has been applied.

As shown in FIG. 5, the improved correlation of PBS elution with plasma viral load also resulted in improved clinical concordance. This is especially notable after a correction factor of 0.6 log is applied.

Example 3

Dried blood spots (DBS) improve access to HIV viral load testing, but yield different results from plasma because of cell-associated viral nucleic acid. The following experiments were performed to assess a free virus elution (FVE) method for preferential elution of plasma-associated virus from DBS samples with phosphate-buffered saline.

Methods:

For the standard COBAS® AmpliPrep/COBAS® TaqMan® (CAP/CTM) Dried Fluid Spot Procedure (DFSP), DBS were extracted with a guanidinium-based sample pre-extraction (SPEX) buffer according to package insert instructions (Roche Molecular Systems. COBAS® AmpliPrep/COBAS® TaqMan® HIV-1 Test Dried Fluid Spot Procedure RUO package insert. Roche Molecular Systems, Pleasanton, Calif., USA). For the Free Virus Elution (FVE) protocol, each DBS was incubated in 1 mL of calcium and magnesium-free phosphate buffered saline (PBS, 154 mM NaCl, 5.6 mM $Na_2HPO_4$, 1.1 mM $KH_2PO_4$, pH 7.4; Corning) in a COBAS® S sample tube at room temperature for >30 min without shaking. The PBS eluate was then directly processed in the S tube (without removing the DBS paper) with the normal TaqMan HIV-1 Test v2.0 workflow, using the dried fluid spot (DFSP) test definition file software (Id.).

The FVE mode of action was explored using a model system of DBS to test HIV-negative blood spiked with (i) purified virus 8E5; (ii) purified RNA from 8E5 virus; or (iii) washed HIV-containing cells from the 8E5 cell line (Folks T M, et al. 1986. Biological and biochemical characterization of a cloned Leu-3-cell surviving infection with the acquired immune deficiency syndrome retrovirus. J Exp Med. 164:280-290). Finally, clinical performance studies used paired DBS and plasma samples from 196 HIV-infected patients (on and off antiretroviral therapy). VL results from clinical samples processed with the FVE method were compared to results from the DFSP protocol with plasma VL measured with the CAP/CTM HIV-1 Test v2.0 as the reference method. For both FVE and DFSP, the assay corrects for the volume difference between a DBS and a plasma specimen. An additional +0.3 log was added to all FVE results for the following reason. FVE is believed to elute only the plasma fraction of blood, which accounts for approximately 50% of a whole blood sample.

Results:

Experiments with spiked samples found that compared to SPEX (which essentially elutes all cell-free and cell-associated viral nucleic acid), PBS elution from DBS is approximately 5 times more selective for cell-free virus than cell-associated HIV nucleic acids. Using PBS elution, consistent and quantitative elution, defined as less than a 0.3 log difference among measurements, was observed with replicate samples over a range of incubation times and temperatures. With incubation times of 0.5, 2 and 12 hours at 23° C., viral loads of 3.10, 3.14 and 3.11 log cp/mL VL were measured, respectively. Comparing 0.5 hour incubations at temperatures of 23, 56 and 70° C., viral loads of 3.38, 3.34 and 3.20 log cp/mL VL were measured, respectively.

As PBS does not confer the RNase inactivation that guanidinium chaotropic buffers provide, sample stability in the presence of high levels of exogenous RNase was assessed. The eluate of a clinical HIV-positive DBS sample was resistant to degradation, with a quantification cycle (Cq) of 31.2 without RNase and a Cq value of 32.9 with RNase. The eluate of an HIV-negative DBS sample spiked with whole virus was also resistant to degradation, with a Cq of 27.4 without RNase and a Cq of 27.1 with RNase. In contrast, the eluate of an HIV-negative DBS sample spiked with naked viral RNA showed a Cq of 22.4 without RNase and a Cq of 34.2 with RNase.

A clinical evaluation of the method used paired DBS and plasma samples from 196 HIV patients, both on and off antiretroviral treatment, with plasma VLs ranging from undetectable to 10⁶ copies/mL. Using plasma viral load as the reference method, the PBS elution method reduced VL over-quantification from DBS as compared to the DFSP protocol (FIG. 6).

Figure 6:
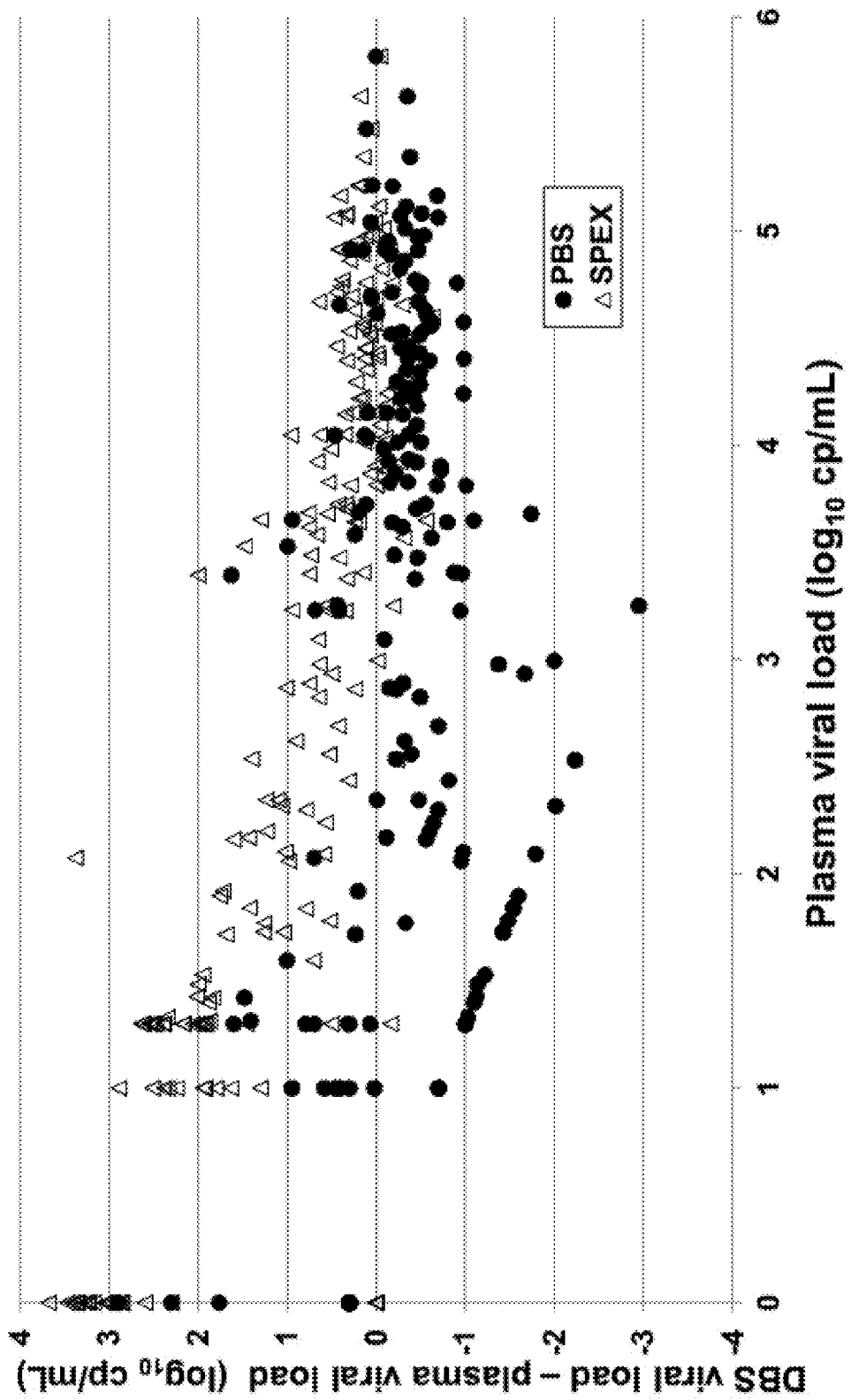
FIG. 6 shows a bias plot comparing DBS viral load methods with plasma viral load as the reference method.

FIG. 6 shows a bias plot comparing DBS viral load methods with plasma viral load as the reference method. The symbols indicate PBS elution (●) and SPEX (guanidinium) elution (Δ). PBS values were adjusted with a +0.3 log volume correction factor. Compared to plasma, PBS had a mean difference of –0.31 $\log_{10}$ copies/mL and a standard deviation of 0.72 $\log_{10}$ copies/mL, while SPEX had a mean difference of +0.94 $\log_{10}$ copies/mL and a standard deviation of 1.07 $\log_{10}$ copies/mL.

With the standard guanidinium SPEX extraction of DBS, the concordance between DBS and plasma at a 1000 cp/mL medical decision point was only 67% due to over-quantified viral loads which mistakenly classified 69% of patients with plasma viral loads below 1000 cp/mL as treatment failures (see Table 3.1 and FIG. 7).

TABLE 3.1

Performance of DFSP protocol at 1000 cp/ml

| | | Plasma | | |
|---|---|---|---|---|
| | | <1000 cp/ml | >1000 cp/ml | |
| DFSP | <1000 cp/ml | 29 | 0 | 29 |
| | >1000 cp/ml | 64 | 103 | 167 |
| | | 93 | 103 | 196 |

SPEX extraction performed with 100% sensitivity and 31% specificity, with a PPV of 62% and an NPV of 100% for virologic failure as defined by plasma viral load.

Figure 7:
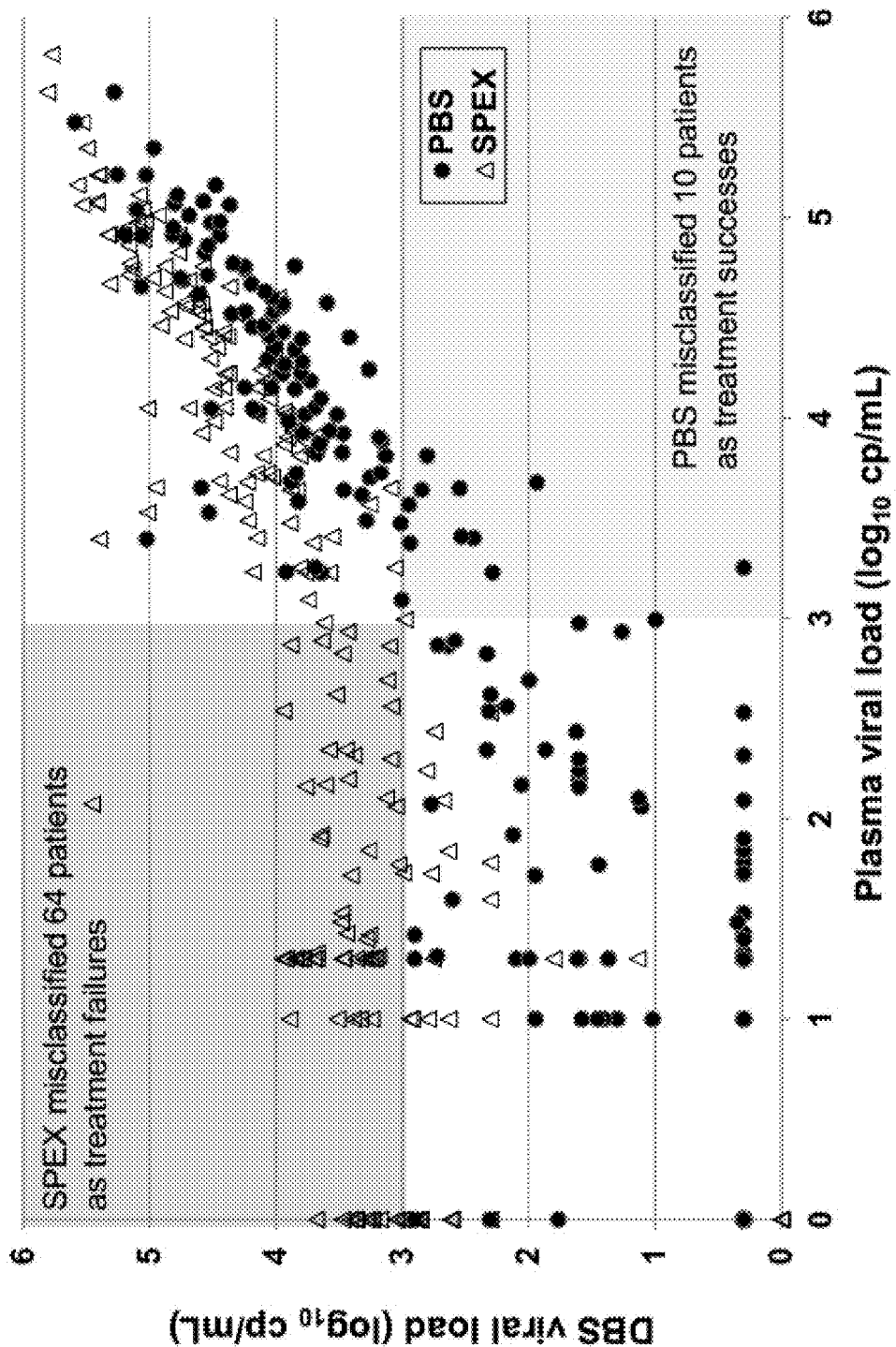
FIG. 7 shows the correlation and concordance of viral load measurements from DBS with plasma.

FIG. 7 shows the correlation and concordance of viral load measurements from DBS with plasma. Symbols indicate PBS elution (●) and SPEX (guanidinium) elution (Δ). PBS values were adjusted with a +0.3 log volume correction factor. Patients who potentially would be misclassified by DBS, using a cutoff viral load of 1000 cp/mL to indicate treatment failure, are indicated by the shaded areas.

With PBS elution, the suppressed patients were all correctly classified, although 10% of patients with viral loads above 1000 cp/mL were now classified as treatment successes (see Table 3.2).

TABLE 3.2

Performance of FVE after volume correction (+0.3 log cp/ml since DBS 50% plasma)

| | | Plasma | |
|---|---|---|---|
| | | <1000 cp/ml | >1000 cp/ml |
| FVE | <1000 cp/ml | 93 | 10 | 103 |
| | >1000 cp/ml | 0 | 93 | 93 |
| | | 93 | 103 | 196 |

Overall DBS concordance with plasma significantly improved to 95% (p<0.05, two-tailed z test). PBS elution performed with 90% sensitivity and 100% specificity, with a PPV of 100% and an NPV of 90% for virologic failure as defined by plasma viral load.

PBS HIV elution of DBS significantly reduced the over-quantification of HIV VL in DBS relative to plasma, when compared to the standard guanidinium extraction protocol. This elution can be executed without additional liquid transfer steps or equipment. Without being bound by any theory, model system experiments suggest that the method works by selectively eluting the free virus component from the sample while the cell-associated HIV nucleic acids are retained on the paper. The addition of RNase A to the PBS did not change virus quantification, suggesting that the RNA template eluted by PBS may be enclosed within protective viral structures. The FVE protocol improved overall percentage agreement for virologic failure, as defined by a plasma VL>1000 cp/mL, from 67% to 95%, and demonstrated a sensitivity of 90% and a specificity of 100% for virologic failure. The use of a PBS elution step to separate free virus from cellular material significantly reduced the over-quantification of HIV VL in DBS.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed:

1. A method for detecting and quantifying cell-free viral nucleic acids from dried blood spots, the method comprising:
   rehydrating a dried blood spot by applying a buffer solution to the dried blood spot to produce a rehydrated dried blood spot;
   optionally fixing cells present in the rehydrated dried blood spot with a fixing reagent to contain cell-associated nucleic acids with the cells;
   eluting cell-free viral nucleic acids from the rehydrated dried blood spot with an eluting reagent that preferentially elutes cell-free nucleic acids without disrupting the cell-associated nucleic acids;
   using a separate filter for further separating the eluted cell-free viral nucleic acids from any cell debris that may be present in the rehydrated dried blood spot; and
   detecting and quantifying the cell-free viral nucleic acids by a nucleic acid quantification technique, wherein the method is performed at ambient temperature.

2. The method of claim 1, wherein the nucleic acid quantification technique is selected from the group consisting of sequence-specific nucleic acid quantification, PCR, isothermal nucleic acid amplification, nucleic acid hybridization, in situ hybridization, and electron microscopy.

3. The method of claim 1, wherein the cell-free viral nucleic acids originate from a virus selected from the group consisting of HIV, HTLV, HCV, HBV, CMV, and EBV.

4. The method of claim 1, wherein the fixing reagent is selected from the group consisting of methanol, ethanol, formaldehyde, chloroform, and acetone.

5. The method of claim 4, wherein the eluting reagent comprises phosphate buffered saline.

6. The method of claim 5, wherein the separation step comprises spin column filtration by centrifugation or vacuum.

7. The method of claim 6, wherein the filter comprises a pore size range between about 0.1 μm to about 100 μm.

8. The method of claim 1, wherein the buffer solution comprises the fixing reagent and the eluting reagent.

9. The method of claim 8, wherein the fixing reagent comprises methanol and the eluting reagent comprises phosphate buffered saline (PBS).

10. The method of claim 1, wherein the buffer solution comprises PBS.

11. The method of claim 1, wherein the buffer solution comprises the eluting reagent.

12. The method of claim 11, wherein the eluting reagent comprises PBS.

13. The method of claim 1, wherein the method is performed at ambient temperature.

14. The method of claim 1, wherein the method is performed in the absence of shaking or vortexing.

15. The method of claim 1, wherein the detecting and quantifying comprises obtaining a viral load titer that is between about 85% and about 99% concordance with a viral load titer from a plasma sample.

* * * * *